(12) United States Patent
Ein-Gal

(10) Patent No.: US 7,559,904 B2
(45) Date of Patent: Jul. 14, 2009

(54) SHOCKWAVE GENERATING SYSTEM

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 606 days.

(21) Appl. No.: 10/620,553

(22) Filed: Jul. 17, 2003

(65) Prior Publication Data

US 2005/0015023 A1    Jan. 20, 2005

(51) Int. Cl.
*A61H 1/00* (2006.01)
(52) U.S. Cl. .............................. 601/2; 601/4
(58) Field of Classification Search .......... 601/15, 601/20, 21, 2–4; 606/127, 128; 604/22, 604/69, 93.01, 95.02; 600/439
See application file for complete search history.

(56) References Cited

U.S. PATENT DOCUMENTS

| | | | | |
|---|---|---|---|---|
| 3,942,531 A | * | 3/1976 | Hoff et al. ..................... | 601/4 |
| 4,617,931 A | * | 10/1986 | Dory ............................. | 601/4 |
| 4,796,613 A | * | 1/1989 | Heumann et al. .............. | 601/4 |
| 4,972,826 A | * | 11/1990 | Koehler et al. ................ | 601/4 |
| 4,976,255 A | * | 12/1990 | Reichenberger et al. ....... | 601/4 |
| 5,058,569 A | * | 10/1991 | Hassler et al. ................. | 601/4 |
| 5,113,848 A | * | 5/1992 | Krauss et al. .................. | 601/4 |
| 5,174,280 A | * | 12/1992 | Gruenwald et al. ............ | 601/4 |
| 5,224,468 A | * | 7/1993 | Grunewald et al. ............ | 601/4 |
| 5,251,630 A | * | 10/1993 | Rattner ....................... | 600/439 |
| 5,279,282 A | * | 1/1994 | Oppelt .......................... | 601/4 |
| 5,309,897 A | * | 5/1994 | Hassler et al. ................ | 601/4 |
| 5,800,365 A | * | 9/1998 | Zhong et al. .................. | 601/4 |
| 7,048,699 B2 | * | 5/2006 | Ein-Gal ........................ | 601/4 |

* cited by examiner

*Primary Examiner*—Brian Casler
*Assistant Examiner*—Amanda L. Lauritzen
(74) *Attorney, Agent, or Firm*—Dekel Patent Ltd.; David Klein

(57) ABSTRACT

A shockwave generating system comprising a first shockwave source device that is formed with an aperture through which a second shockwave source device is adapted to transmit shockwaves. The second shockwave source device may be disposed at least partially in the aperture.

11 Claims, 3 Drawing Sheets

SHOCKWAVE GENERATING SYSTEM

FIELD OF THE INVENTION

The present invention relates to extracorporeal shockwave treatment (ESWT) in general, and particularly to a shockwave generating system that includes a first shockwave source device, which is formed with an aperture for a second shockwave source device.

BACKGROUND OF THE INVENTION

Extracorporeal shockwave treatment (ESWT) is an extracorporeal treatment modality for a variety of applications including disintegration of urinary tract calculi, disintegration of any stone-like concretions or depositions of minerals and salts found in ducts, blood vessels or hollow organs of a patient's body, advancing bone union by causing micro-fractures and relieving pain associated with tendons, joints and bony structures. A shockwave device is a device used to perform ESWT, which includes a shockwave source typically comprising an electrical-to-shockwave energy converter and a focusing mechanism for directing shockwaves energy to treated area. Electro-hydraulic, electromagnetic and piezoelectric are some of the technologies utilized for energy conversion while focusing is accomplished via acoustic lenses or via ellipsoidal, parabolic or other shaped reflector. Typically, a shockwave focusing mechanism is cylindrically symmetric about an axis defining the shockwave propagation axis.

One well-known example of ESWT is extracorporeal shockwave lithotripsy (ESWL), which is an extra-corporeal treatment modality for disintegration of calculi, such as kidney stones, stone-like concretions in ducts or hollow organs, and other brittle deposits in the body. A lithotripter is a device used to perform ESWL, which includes a shockwave head coupled to a patient's body, in order to deliver shockwave energy to disintegrate the calculi.

The prior art may be classified according to the geometry of the acoustic wave generation and associated focusing: point source and ellipsoidal reflector, planar source and acoustic lens, cylindrical source and parabolic reflector, and spherical source with no additional focusing. The prior art typically converts electrical energy into acoustic waves, such as by generating a strong pulse of an electric or magnetic field, usually by a capacitor discharge, and then converting the electromagnetic field into acoustic energy.

Point sources for the generation of acoustic waves in a lithotripter are described in various patents, such as U.S. Pat. Nos. 3,942,531 and 4,539,989, for example, the disclosures of which are incorporated herein by reference. A point source typically comprises electrohydraulic apparatus. Fast discharges of electrical energy between tips of closely spaced electrodes give rise to a sequence of spherical waves in a propagating liquid. The electrodes are arranged with respect to an ellipsoidal reflector, which has two focal points. The electrical energy is discharged at the first focus, and the waves are focused onto the second focus.

A planar source typically comprises electromagnetic apparatus. A thin circular membrane applies pressure to the propagation liquid by being jolted or repelled away from a planar coil. Fast discharges of electrical energy into the coil and the associated rapid changes in the magnetic field induce currents in the membrane, turning it into a magnet with a polarization opposite to that of the coil. The ensuing repulsions of the membrane, which is in close contact with the propagating liquid, generate the acoustic waves. U.S. Pat. No. 4,674,505, the disclosure of which is incorporated herein by reference, describes an example of such a planar source with an associated acoustic lens.

Apparatus incorporating a cylindrical source uses an electromagnetic approach similar to that used for the planar source. A coil is mounted on a cylindrical support and a cylindrical membrane, being pushed or repelled radially, gives rise to outwardly propagating cylindrical waves. A parabolic reflector focuses the waves into a point on the cylindrical axis of the system. Cylindrical sources enable using an in-line ultrasonic probe for imaging the focal area. Examples of cylindrical sources are described in U.S. Pat. No. 5,058,569 to Hasssler et al., assigned to Siemens Aktiengesellschaft (Munich, Germany) and U.S. Pat. No. 5,174,280 to Gruenwald et al., assigned to Dornier Medizintechnik GmbH (Germering, Germany), the disclosures of which are incorporated herein by reference.

Spherical waves are generated by an array of piezo-electric transducers or by an electromagnetic approach with a spherical membrane being repulsed inwardly into the propagating liquid. No further focusing is required. Spherical sources are mentioned in the background of U.S. Pat. No. 5,174,280.

Each of the prior art acoustic wave generation and focusing apparatus has limitations. Acoustic wave generators generate shocks at a rate of one or two shocks per second, whereas extracorporeal shockwave treatment (ESWT) typically requires thousands of shocks per treatment. The electrohydraulic approach suffers from the disadvantages of non-uniform discharges, pain and high noise level. The electromagnetic planar approach suffers from the disadvantages of high cost and complexity in manufacturing the coil and lens assembly. Acoustic lenses for planar sources are fragile and non-effective for large apertures. In addition to the complexity of manufacturing electromagnetic cylindrical sources, the parabolic reflector is not highly efficient because the source is in the way of reflected waves adjacent thereto. The piezoelectric array is expensive to manufacture, and it is difficult to obtain high-level, well-distributed intensities. The array requires a relatively large aperture that prevents access for x-ray imaging of the focal area.

SUMMARY OF THE INVENTION

The present invention seeks to provide an improved shockwave generating system. The shockwave generating system may include a first shockwave source device, which is formed with an aperture for a second shockwave source device, as is described more in detail hereinbelow. The invention may significantly increase the versatility of treatment plans in lithotripsy, for example. However, the invention is not limited to shockwave generation and may be employed for any kind of energy source, such as but not limited to, electromagnetic wave energy.

There is thus provided in accordance with an embodiment of the invention a shockwave generating system comprising a first shockwave source device that is formed with an aperture through which a second shockwave source device is adapted to transmit shockwaves. The second shockwave source device may be disposed at least partially in the aperture. The first shockwave source device may be axisymmetric, and the aperture may be formed on an axis of symmetry of the first shockwave source device.

In accordance with an embodiment of the invention an axis of wave propagation of the first shockwave source device may or may not be generally coaxial with an axis of wave propagation of the second shockwave source device.

Further in accordance with an embodiment of the invention the first and second shockwave source devices may be arranged with respect to one another to focus on a common focus or on different foci.

Still further in accordance with an embodiment of the invention the first and second shockwave source devices may each comprise a membrane, a propagation medium and an excitation device that moves the membrane to generate a shockwave that propagates in the propagation medium, wherein the propagation media of the first and second shockwave source devices may or may not be the same.

In accordance with an embodiment of the invention one or both of the first and second shockwave source devices may comprise at least one of an electrohydraulic shockwave source device, an electromagnetic shockwave source device and a piezoelectric shockwave source device.

Further in accordance with an embodiment of the invention one or both of the first and second shockwave source devices may comprise at least one of a spherical shockwave source device, a planar shockwave source device, a point shockwave source device, a conical shockwave source device and a cylindrical shockwave source device.

In accordance with an embodiment of the invention a focusing device may be provided that focuses shockwaves from the first and/or second shockwave source device to a focus.

Still further in accordance with an embodiment of the invention a controller may be provided that triggers the first and second shockwave source devices in synchrony or asynchrony.

BRIEF DESCRIPTION OF THE DRAWINGS

The present invention will be understood and appreciated more fully from the following detailed description taken in conjunction with the drawings in which.

DETAILED DESCRIPTION OF AN EMBODIMENT

Figure 1:
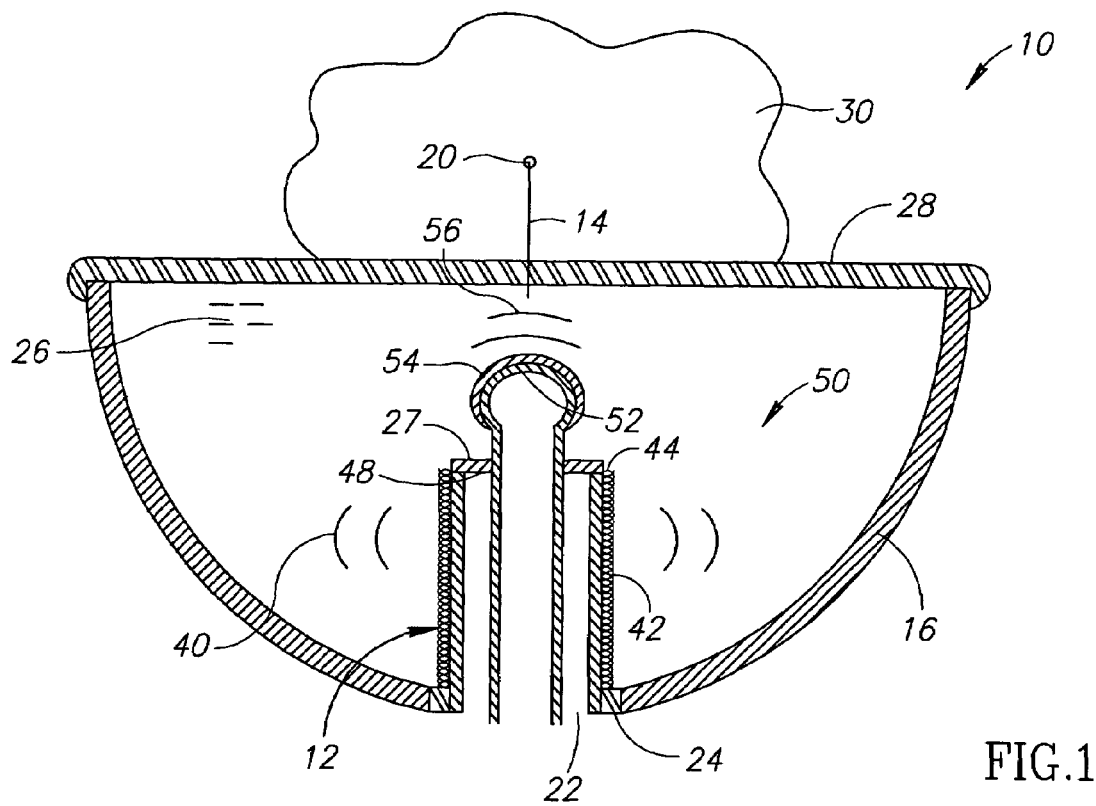
FIG. 1 is a simplified sectional illustration of a shockwave generating system constructed and operative in accordance with an embodiment of the invention.

Reference is now made to FIG. 1, which illustrates a shockwave generating system 10, constructed and operative in accordance with an embodiment of the present invention.

Shockwave generating system 10 comprises a first shockwave source device 12, which in the illustrated embodiment of FIG. 1, includes a cylindrical acoustic wave transducer with a longitudinal axis of symmetry 14. However, it is emphasized that the cylindrical transducer is just one example of carrying out the invention, and the invention is not limited to this geometry or type of transducer. A modified parabolic reflector comprising an at least partially parabolic reflector 16 may be arranged with respect to first shockwave source device 12 so as to focus an acoustic wave 40 emanating from device 12. Reflector 16 may be an axisymmetric reflector. More specifically, reflector 16 may be constructed of a portion of parabola revolved symmetrically about the longitudinal symmetry axis 14 so that outwardly radiated acoustic waves 40 from first shockwave source device 12 are reflected by reflector 16 towards a focus 20, preferably situated on axis 14. First shockwave source device 12 may fit in an aperture 22 formed in reflector 16, and may be sealed thereat by a sealing ring 24. Aperture 22 may be formed on axis 14 of reflector 16.

The inner volume of reflector 16 may be filled with a propagation medium 26 (e.g., a liquid, such as water). An open end 48 of first shockwave source device 12 may be covered with a membrane 27 in order to seal the inside of first shockwave source device 12 from ingress therein of propagation medium 26. The end face of reflector 16 may be covered with another membrane 28. Shockwave generating system 10 may be placed against or near a target 30, which it is desired to treat. Acoustic waves 40 generated by first shockwave source device 12 may propagate towards focus 20, located in target 30, via propagating medium 26 and through membrane 28. Axis 14 is thus preferably also the shockwave propagation axis.

The acoustic waves 40 may be produced in a variety of manners, such as but not limited to, by means of a membrane 44 and an excitation device 42, such as a coil wound on a cylindrical support of first shockwave source device 12. Excitation device 42 moves or vibrates membrane 44 to generate shockwaves 40 that propagate in propagation medium 26. Other suitable excitation devices 42 include, but are not limited to, an electromagnetic, an electrohydraulic or a piezoelectric shockwave head that pulses membrane 44.

A second shockwave source device 50 may be disposed in aperture 22 (and may sealingly pass through membrane 27). In the illustrated embodiment, second shockwave source device 50 may comprise a spherical acoustic wave transducer, which may include one or more piezoelectric or electromagnetic transducers 52 that repulse a spherical membrane 54 to produce shockwaves 56 in propagating medium 26. In the case of a spherical transducer, the shockwaves 56 may not require further focusing and propagate towards target 30 and focus 20. The invention is not limited, however, to a spherical transducer.

Figure 2:
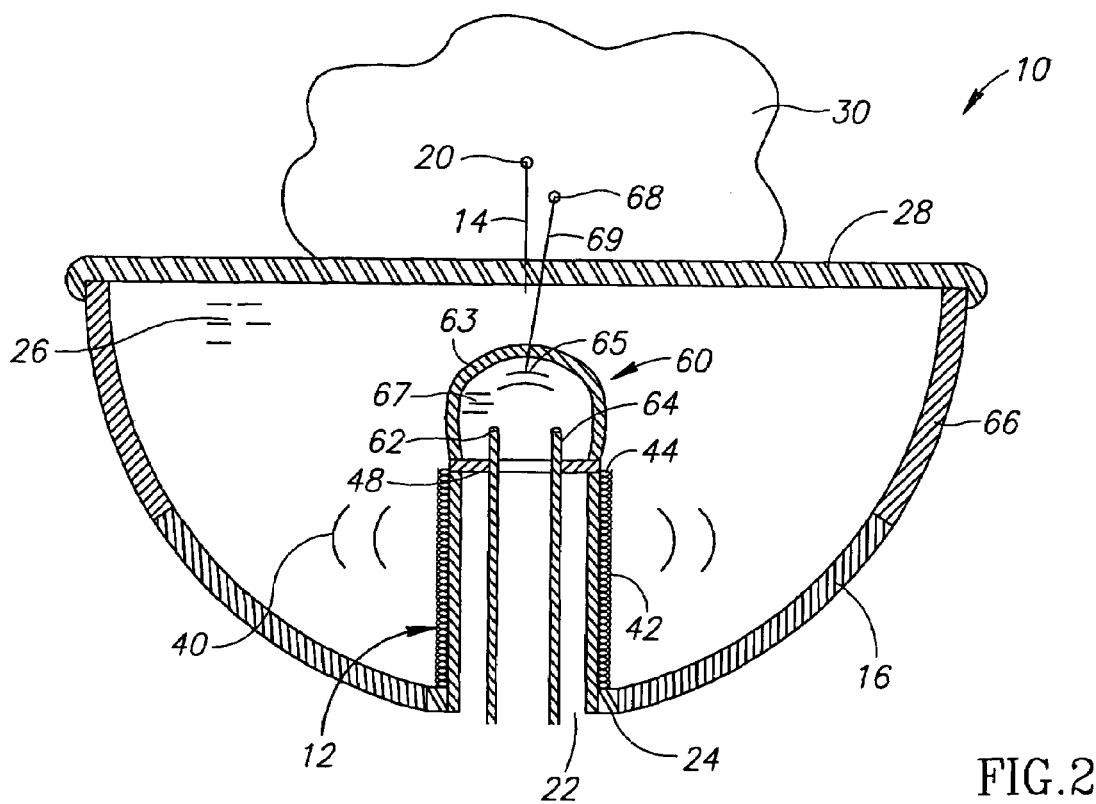
FIG. 2 is a simplified sectional illustration of a shockwave generating system constructed and operative in accordance with another embodiment of the invention.

Reference is now made to FIG. 2, which illustrates an alternate construction of shockwave generating system 10. In the embodiment of FIG. 2, a second shockwave source device 60 may comprise one or more point sources 62, wherein fast discharges of electrical energy between tips of closely spaced electrodes 64 give rise to a sequence of spherical waves 65 in a propagating medium 67. Propagating medium 67 may be separated from propagating medium 26 by a secondary membrane 63. Propagating medium 67 may be the same or different from propagating medium 26. Electrodes 64 may be arranged with respect to a reflector 66, e.g., an elliptical reflector, which focuses the shockwaves 65 onto a second focus 68 along a propagation axis 69.

A comparison of the exemplary embodiments of FIGS. 1 and 2 illustrates some of the versatility of the present invention.

For example, in the embodiment of FIG. 1, the axis of wave propagation of first shockwave source device 12 is generally coaxial with an axis of wave propagation of second shockwave source device 50. In contrast, in the embodiment of FIG. 2, the axes of wave propagation of first and second shockwave source devices 12 and 60 are generally not coaxial.

In the embodiment of FIG. 1, first and second shockwave source devices 12 and 50 are arranged with respect to one another to focus on common focus 20. In contrast, in the embodiment of FIG. 2, first and second shockwave source devices 12 and 60 are arranged with respect to one another to focus on different foci.

In the embodiment of FIG. 1, the propagation media of first and second shockwave source devices 12 and 50 are the same. In contrast, in the embodiment of FIG. 2, the propagation media of first and second shockwave source devices 12 and 60 may be different.

Figure 3:
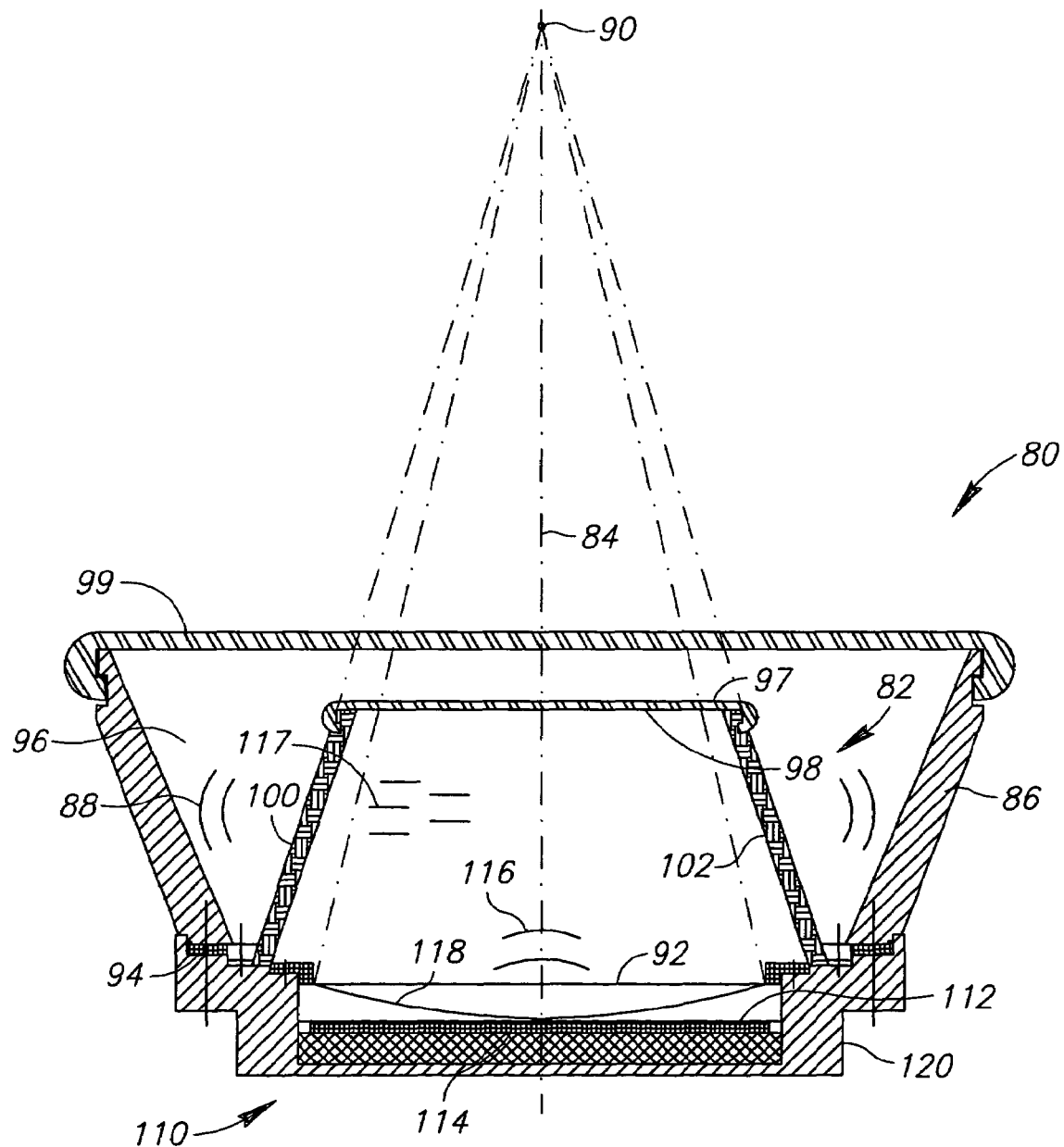
FIG. 3 is a simplified sectional illustration of a shockwave generating system constructed and operative in accordance with yet another embodiment of the invention.

Reference is now made to FIG. 3, which illustrates a shockwave generating system 80, constructed and operative in accordance with an embodiment of the present invention.

Shockwave generating system 80 comprises a first shockwave source device 82, which in the illustrated embodiment of FIG. 3, includes a conical acoustic wave transducer with a longitudinal axis of symmetry 84. However, it is emphasized that the conical transducer is just one example of carrying out the invention, and the invention is not limited to this geometry or type of transducer. A modified parabolic reflector comprising an at least partially parabolic reflector 86 may be arranged with respect to first shockwave source device 82 so as to focus an acoustic wave 88 emanating from device 82. Reflector 86 may be an axisymmetric reflector. More specifically, reflector 86 may be constructed of a portion of parabola revolved symmetrically about the longitudinal symmetry axis 84 so that outwardly radiated acoustic waves 88 from first shockwave source device 82 are reflected by reflector 86 towards a focus 90, preferably situated on axis 84. First shockwave source device 82 may fit in an aperture 92 formed in reflector 86, and may be sealed thereat by a sealing ring 94. Aperture 92 may be formed on axis 84 of reflector 86.

The inner volume of reflector 86 may be filled with a propagation medium 96 (e.g., a liquid, such as water). An open end 98 of first shockwave source device 82 may be covered with a membrane 97 in order to seal the inside of first shockwave source device 82 from ingress therein of propagation medium 86. The end face of reflector 86 may be covered with another membrane 99. Acoustic waves 88 generated by first shockwave source device 82 may propagate towards focus 90, via propagating medium 96 and through membrane 99. Axis 84 is thus preferably also the shockwave propagation axis.

The acoustic waves 88 may be produced in a variety of manners, such as but not limited to, by means of a membrane 100 and an excitation device 102, such as a coil wound on a conical support of first shockwave source device 82. Excitation device 102 moves or vibrates membrane 100 to generate shockwaves 88 that propagate in propagation medium 96. Other suitable excitation devices 102 include, but are not limited to, an electromagnetic, an electrohydraulic or a piezoelectric shockwave head that pulses membrane 100.

A second shockwave source device 110 may be disposed in aperture 92. In the illustrated embodiment, second shockwave source device 110 may comprise a planar acoustic wave transducer, which may include a membrane 112 and an excitation device 114, such as a coil in juxtaposition with membrane 112. Excitation device 114 moves or vibrates membrane 112 to generate shockwaves 116 that propagate in propagation medium 117, which may or may not be the same as propagation medium 96. A focusing device 118, such as but not limited to, a concave lens may focus shockwaves 116 to focus 90. An end cap 120 may secure and seal second shockwave source device 110 to the rest of shockwave generating system 80.

Figure 4:
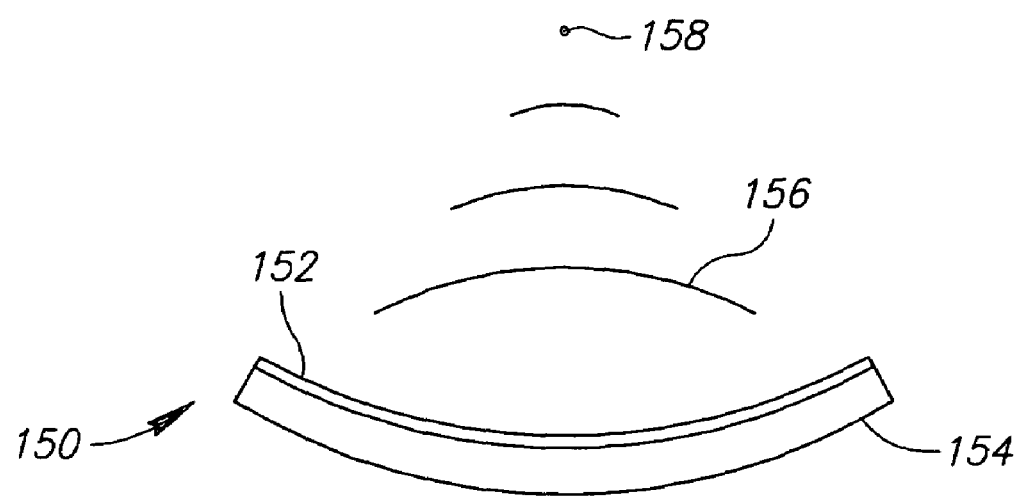
FIG. 4 is a simplified sectional illustration of a shockwave source device constructed and operative in accordance with an embodiment of the invention.

Reference is now made to FIG. 4, which illustrates a shockwave source device 150, constructed and operative in accordance with an embodiment of the present invention. Instead of the planar acoustic wave transducer used for second shockwave source device 110 shown in FIG. 3, shockwave source device 150 may comprise an excitable member, such as but not limited to, a membrane 152, and an excitation device 154, such as a coil in juxtaposition with membrane 152. Membrane 152 and excitation device 154 may be shaped in the form of a three-dimensional curved surface, such as but not limited to, a partial spheroid, partial ellipsoid and/or partial paraboloid. Excitation device 154 moves or vibrates membrane 152 to generate shockwaves 156 that are focused to a focus 158 due to the geometric shape of membrane 152 and excitation device 154 without the need for a focusing device.

Figure 5:
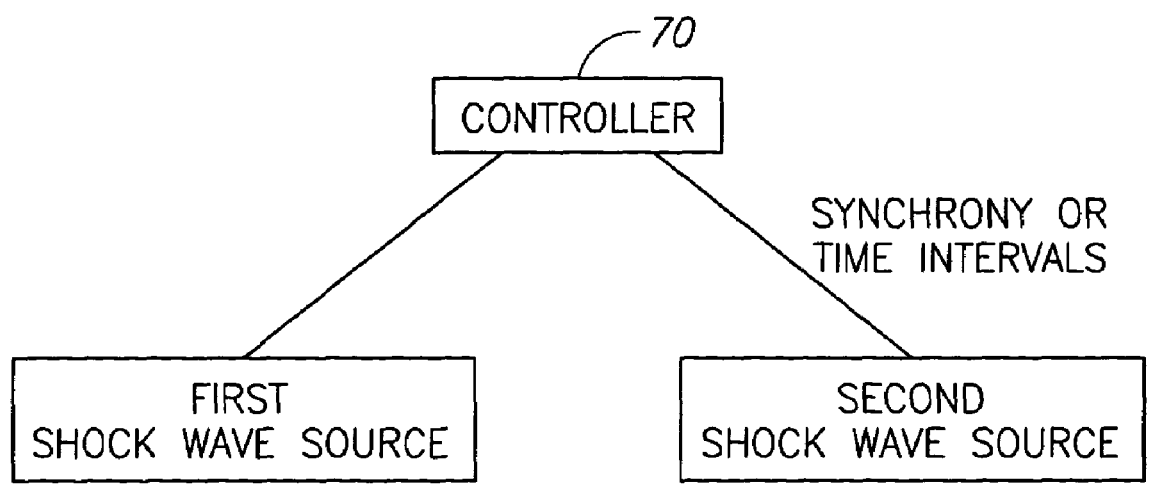
FIG. 5 is a simplified a block diagram of the shockwave generating system of FIGS. 1, 2 or 3, in accordance with an embodiment of the invention.

Reference is now made to FIG. 5, which illustrates a block diagram of shockwave generating system 10 or 80 of FIGS. 1, 2 or 3. The shockwave generating system may comprise a controller 70 coupled to the first and second shockwave source devices that coordinates their operation. For example, controller 70 may trigger the first and second shockwave source devices in synchrony or at different time intervals.

Suitable imaging apparatus (not shown) may be provided, such as but not limited to, a fluoroscope or an ultrasonic probe inserted through some aperture in, or adjacent to, the shockwave generating system.

As mentioned hereinabove, the invention is not limited to shockwave generation and may be employed for any kind of energy source, such as but not limited to, electromagnetic wave energy. Accordingly, throughout the specification and claims, the terms "shockwave source" and "shockwave generation" do not just refer to acoustic shockwaves, but also encompass any kind of energy source or energy generation.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A shockwave generating system comprising:
   a first shockwave source device comprising an acoustic wave transducer with a longitudinal axis of symmetry;
   a reflector which is axisymmetric about said longitudinal axis of symmetry;
   a propagation medium that fills an inner volume of said reflector, said acoustic wave transducer being separated from said reflector by the propagation medium, wherein said reflector is arranged with respect to said first shockwave source device so that outwardly radiated acoustic waves from said first shockwave source device propagate in the propagation medium and are reflected by a reflective surface of said reflector towards a focus, said first shockwave source device fitting in an aperture which is formed in said reflector and located on said longitudinal axis of symmetry, said aperture being sealed by a sealing ring;
   a first membrane that covers an open end of said first shockwave source device non-parallel to said longitudinal axis of symmetry in order to seal said first shockwave source device from ingress therein of the propagation medium, said first membrane being shaped differently from the reflective surface of said reflector;
   a second membrane that covers an end face of said reflector; and
   a second shockwave source device disposed in said aperture and adapted to emit acoustic waves, wherein said second shockwave source device sealingly passes through said first membrane.

2. The shockwave generating system according to claim 1, wherein said reflector comprises an at least partially parabolic reflector.

3. The shockwave generating system according to claim 1, wherein first shockwave source device comprises a cylindrical acoustic wave transducer comprising an excitable membrane and an excitation device operative to move said excitable membrane to generate shockwaves that propagate in said propagation medium.

4. The shockwave generating system according to claim 1, wherein said second shockwave source device comprises a spherical acoustic wave transducer, which repulse a spherical membrane to produce shockwaves in the propagating medium.

5. The shockwave generating system according to claim 4, wherein said spherical membrane has a rounded portion that curves outwards towards and points to said second membrane that covers the end face of said reflector.

6. The shockwave generating system according to claim 1, wherein said first and second shockwave source devices are arranged with respect to one another to focus on a common focus.

7. The shockwave generating system according to claim 1, wherein said first and second shockwave source devices are arranged with respect to one another to focus on different foci.

8. The shockwave generating system according to claim 1, wherein first shockwave source device comprises a conical acoustic wave transducer comprising an excitable membrane and an excitation device operative to move said excitable membrane to generate shockwaves that propagate in said propagation medium.

9. The shockwave generating system according to claim 1, wherein said second shockwave source device comprises a planar acoustic wave transducer comprising an excitable membrane and an excitation device operative to move said excitable membrane to generate shockwaves that propagate in said propagation medium, and a focusing lens adapted to focus these shockwaves to a focus.

10. The shockwave generating system according to claim 1, wherein said first membrane is planar and generally perpendicular to said longitudinal axis of symmetry.

11. The shockwave generating system according to claim 1, wherein said second shockwave source device comprises one or more point sources, wherein fast discharges of electrical energy between tips of closely spaced electrodes give rise to a sequence of spherical waves in the propagating medium.

* * * * *